United States Patent
Harding et al.

(10) Patent No.: US 9,069,181 B2
(45) Date of Patent: Jun. 30, 2015

(54) OPTICAL IMAGING SYSTEM AND METHOD, AND APERTURE STOP ASSEMBLY AND APERTURE ELEMENT

(71) Applicant: General Electric Company, Shelton, CT (US)

(72) Inventors: Kevin George Harding, Niskayuna, NY (US); Guiju Song, Niskayuna, NY (US); Tao Li, Niskayuna, NY (US); Dongmin Yang, Niskayuna, NY (US); Jie Han, Niskayuna, NY (US); Zirong Zhai, Niskayuna, NY (US)

(73) Assignee: General Electric Company, Schenectady, CT (US)

( * ) Notice: Subject to any disclaimer, the term of this patent is extended or adjusted under 35 U.S.C. 154(b) by 0 days.

(21) Appl. No.: 13/630,373

(22) Filed: Sep. 28, 2012

(65) Prior Publication Data
US 2013/0083386 A1    Apr. 4, 2013

(30) Foreign Application Priority Data

Sep. 29, 2011    (CN) .......................... 2011 1 0293452

(51) Int. Cl.
*G02F 1/01*    (2006.01)
*G02B 5/30*    (2006.01)
(Continued)

(52) U.S. Cl.
CPC .............. *G02B 27/283* (2013.01); *G01N 21/21* (2013.01); *A61B 5/0059* (2013.01); *A61B 2560/0223* (2013.01); *A61B 1/00186* (2013.01); *A61B 1/045* (2013.01)

(58) Field of Classification Search
CPC .... G02B 27/283; G01N 21/21; A61B 5/0059; A61B 2560/0223

USPC ........ 359/240, 483.01, 437, 485.03, 894, 900
See application file for complete search history.

(56) References Cited

U.S. PATENT DOCUMENTS

| 4,015,221 A | 3/1977 | Dalton |
| 5,964,696 A | 10/1999 | Mihalca et al. |

(Continued)

FOREIGN PATENT DOCUMENTS

| CN | 102073264 A | 5/2011 |
| EP | 2515100 A1 | 10/2012 |
| JP | 2009020413 A | 1/2009 |

OTHER PUBLICATIONS

Quality Crystal and Optics for Laser Applications (Mar. 30, 2010), Red Optronics, http://www.redoptronics.com/glan-thompson-polarizer.html.*

(Continued)

*Primary Examiner* — Tuyen Tra
(74) *Attorney, Agent, or Firm* — Mark A. Conklin; GE Global Patent Operation

(57) ABSTRACT

An optical imaging system includes a birefringent element, a light modulating element, and a polarizer element. The birefringent element is configured for decomposing un-polarized light into first linear polarized light and second linear polarized light under different refractive indexes to respectively form a first focal length and a second focal length in the optical imaging system. The light modulating element is configured for modulating a state of polarization of the first and second linear polarized light in response to control signals. The polarizer element is configured for filtering out one of the modulated first and second linear polarized light for creating a single image.

20 Claims, 13 Drawing Sheets

(51) Int. Cl.
  *G02B 27/28* (2006.01)
  *G01N 21/21* (2006.01)
  *A61B 1/00* (2006.01)
  *A61B 1/045* (2006.01)
  *A61B 5/00* (2006.01)

(56) References Cited

U.S. PATENT DOCUMENTS

| | | | |
|---|---|---|---|
| 6,549,231 | B1 | 4/2003 | Matsui |
| 6,624,935 | B2 | 9/2003 | Weissman et al. |
| 7,394,498 | B2 | 7/2008 | Takaoka |
| 7,762,466 | B2 | 7/2010 | Tan et al. |
| 2006/0170901 | A1 | 8/2006 | Tanitsu et al. |
| 2010/0053361 | A1 | 3/2010 | Sugita et al. |
| 2010/0079658 | A1 | 4/2010 | Ohara et al. |
| 2011/0122281 | A1 | 5/2011 | Ohara et al. |
| 2011/0157496 | A1 | 6/2011 | Im |

OTHER PUBLICATIONS

Search Report from GB Application No. 1216954.6 dated Jun. 26, 2013.
Combined search and examination report from GB Application No. 1216954.6 dated Jan. 24, 2013.

* cited by examiner

OPTICAL IMAGING SYSTEM AND METHOD, AND APERTURE STOP ASSEMBLY AND APERTURE ELEMENT

BACKGROUND

Embodiments of the invention relate generally to an optical imaging system and more particularly to an optical imaging system having the capability of changing to multiple focal lengths with polarization light.

Inspection devices including borescopes, videoscopes, fiberscopes, and endoscopes are non-destructive evaluation (NDE) tools widely used in industrial applications and medical applications. The inspection devices are often used to inspect inaccessible locations for damage or wear or to verify whether parts have been properly manufactured or assembled. The inspection devices may employ an external light source coupled to fiber optic bundles or a light source, such as light-emitting diode (LED), placed at the device's distal end to provide illumination of a target. When the target is illuminated, an image of the target is formed by a lens system on an image sensor, and the image is relayed to a display such as a video screen. In order to inspect a large range of field, the lens system in front of the image sensor with a fixed focal length needs to be designed to achieve a large depth of field (DOF). However, a larger DOF lens will result in a darker image due to the smaller aperture stop used. Such darker images may result in inspection failures or difficulties. Typically, a set of a variety DOF tips with different lenses are used in inspection devices with some tips offering near field inspection and the other tips being used for mid to far field inspection. However, repeatedly changing the tips is time-consuming and may decrease the inspection efficiency and user convenience.

Therefore, it is desirable to provide an inspection device and method of operating the inspection device to address the above-mentioned problems.

BRIEF DESCRIPTION

In accordance with embodiments disclosed herein, an optical imaging system for use within an inspection device is provided. The optical imaging system includes a birefringent element, a light modulating element, and a polarizer element. The birefringent element is configured for decomposing un-polarized light into first linear polarized light and second linear polarized light under different refractive indexes to respectively form a first focal length and a second focal length in the optical imaging system. The light modulating element is configured for modulating a state of polarization of the first and second linear polarized light in response to control signals. The polarizer element is configured for filtering out one of the modulated first and second linear polarized light for creating a single image.

In accordance with embodiments disclosed herein, a method for providing multiple focal lengths for inspecting a target having variable positions with respect to an optical imaging system employed in an inspection device is also provided. The method includes decomposing un-polarized light reflected or diffused from the target into first linear polarized light and second linear polarized light under different refractive indexes to respectively form a first focal length and a second focal length in the optical imaging system; modulating a state of polarization of the first and second linear polarized light in response to control signals; and filtering out one of the modulated first and second linear polarized light for creating a single image.

In accordance with embodiments disclosed herein, an aperture stop assembly using as a two-mode aperture stop element without mechanical control is further provided. The aperture stop assembly includes an aperture element, a light modulating element, and a polarizer element. The aperture element includes a polarizer part and defines an aperture part in the center of the aperture element. The polarizer part is configured for filtering out linear polarized light in a first fixed state of polarization. The light modulating element is configured for modulating a state of polarization of linear polarized light in response to control signals. The polarizer element is configured for filtering out linear polarized light in a second fixed state of polarization. The light modulating element is located between the aperture element and the polarizer element.

In accordance with embodiments disclosed herein, an aperture element used in the aperture stop assembly is provided. The aperture element includes a polarizer part and defines an aperture part in the center of the polarizer part. The polarizer part is configured for filtering out linear polarized light in a fixed state of polarization.

DRAWINGS

These and other features, aspects, and advantages of the present disclosure will become better understood when the following detailed description is read with reference to the accompanying drawings in which like characters represent like parts throughout the drawings, wherein.

Figure 5:
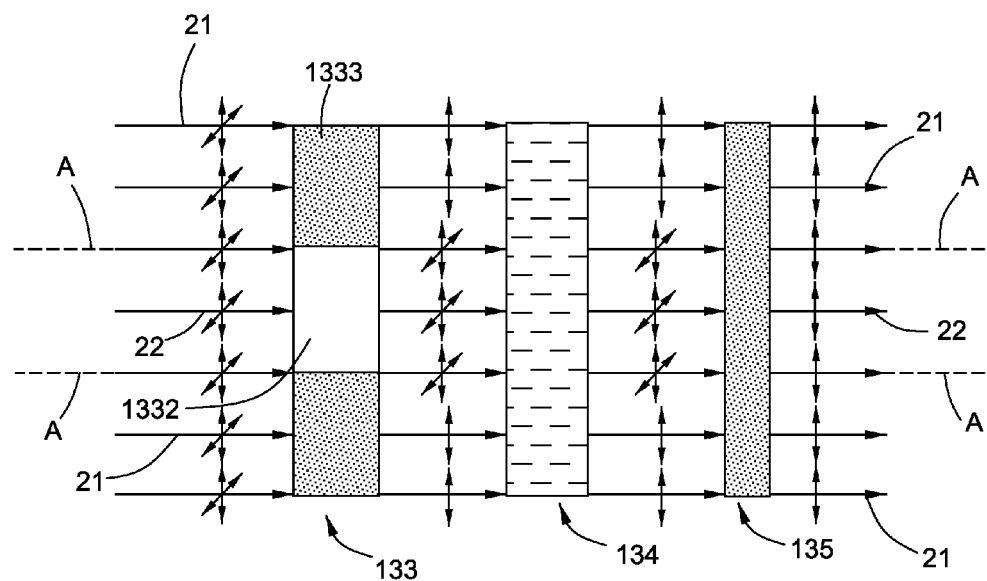
FIGS. 5 and 6 are schematic views to show two working states of an aperture stop assembly, each in accordance with an exemplary embodiment wherein the aperture stop assembly includes an aperture element, a light modulating element, and a polarizer element.
Figure 6:
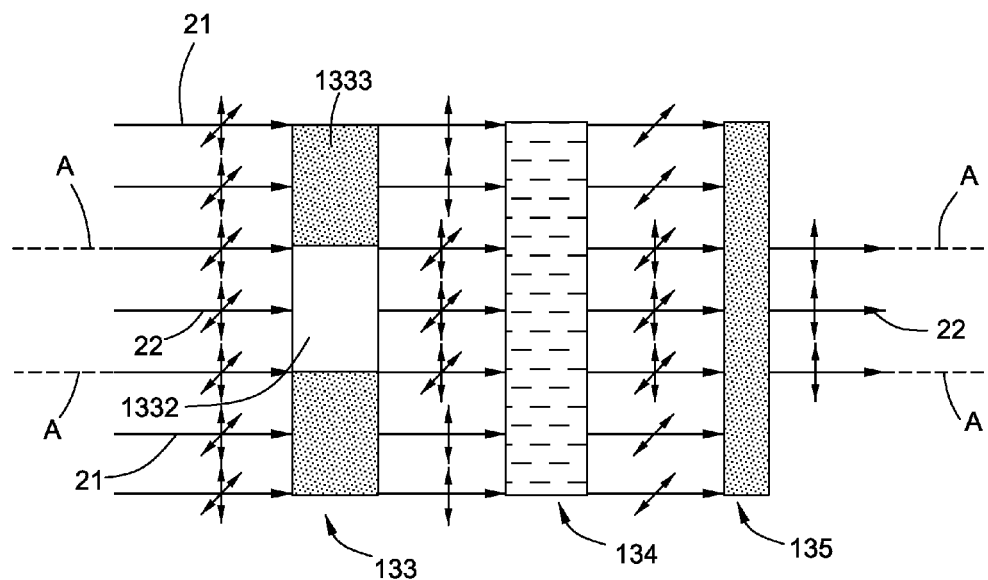
Figure 7:
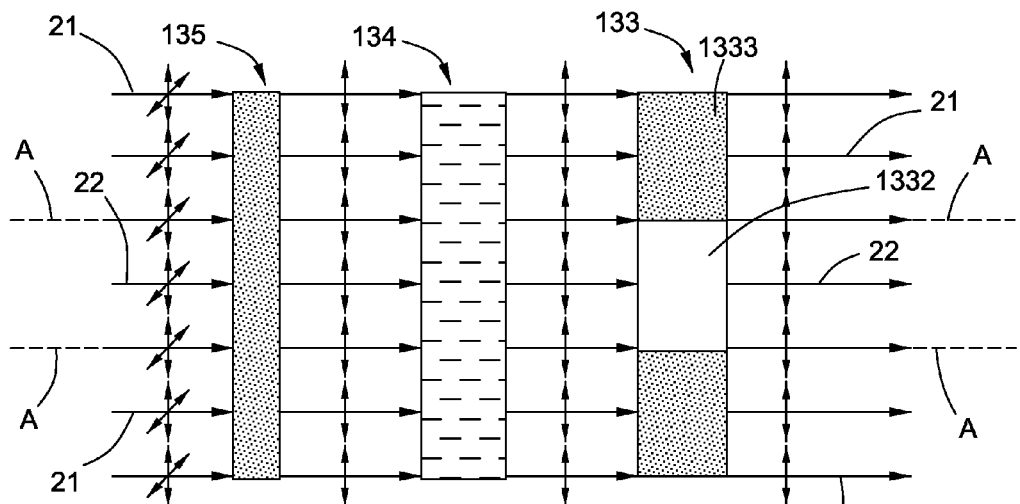
Figure 8:
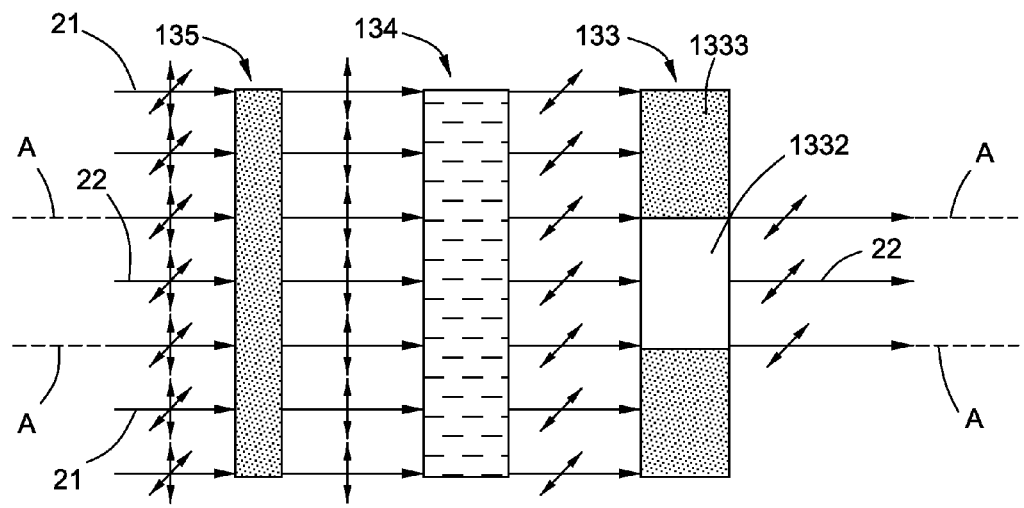

FIGS. 7 and 8 are schematic views to show two working states of an aperture stop assembly, each in accordance with an exemplary embodiment, wherein the incident direction of light of FIGS. 7 and 8 is opposite to the incident direction of light of FIGS. 5 and 6.

Figure 9:
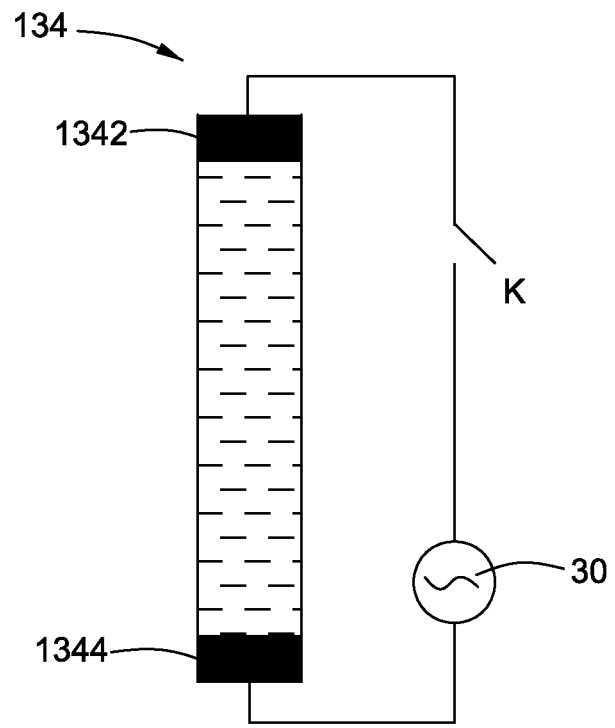
Figure 10:
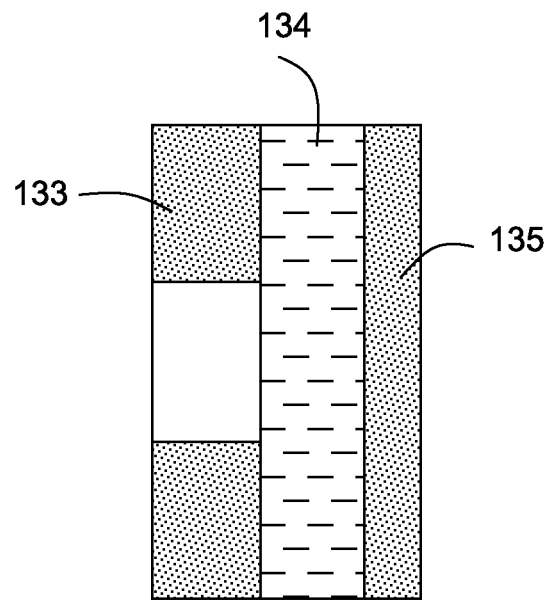

FIG. 9 is a schematic control circuit diagram for the light modulating element of the aperture stop assembly of FIGS. 5-8 in accordance with one embodiment.

FIGS. 10-13 show four different arrangements of the aperture stop assembly of FIGS. 5-8 in accordance with one embodiment, respectively.

Figure 14:
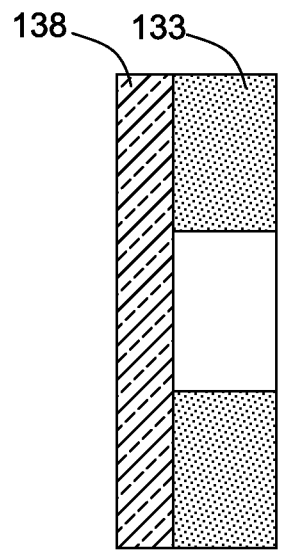
Figure 15:
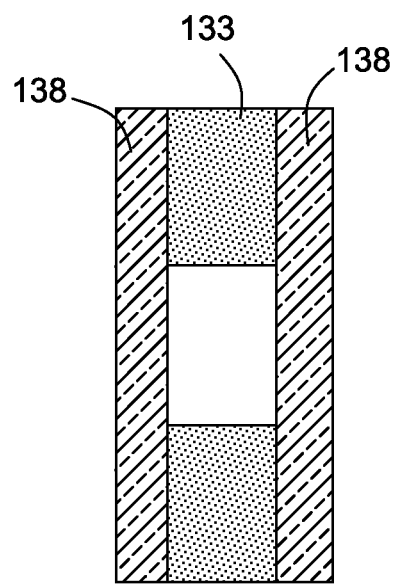
Figure 16:
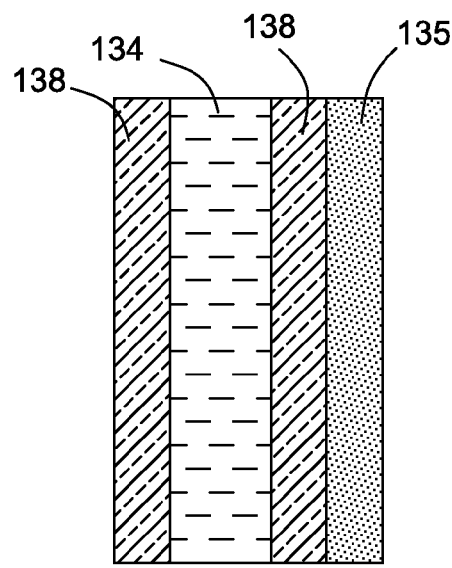

FIGS. 14-16 show elements of the aperture stop assembly of FIGS. 5-8, together with transparent substrates.

Figure 17:
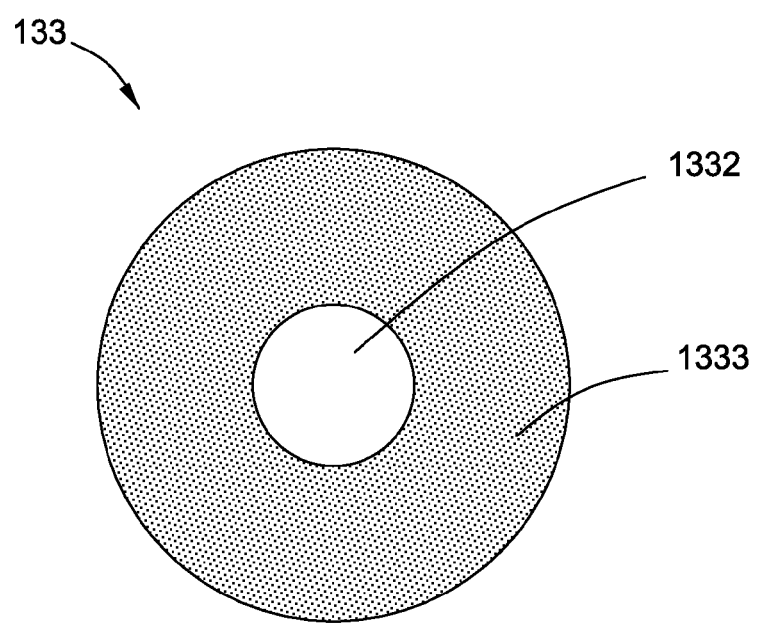

FIG. 17 is a schematic front view of the aperture element of the aperture stop assembly of FIGS. 5-8 in accordance with one embodiment.

Figure 18:
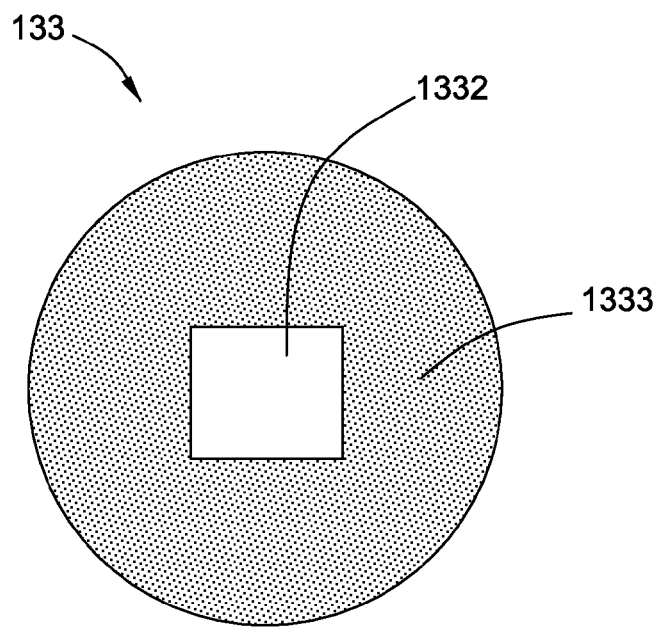
Figure 19:
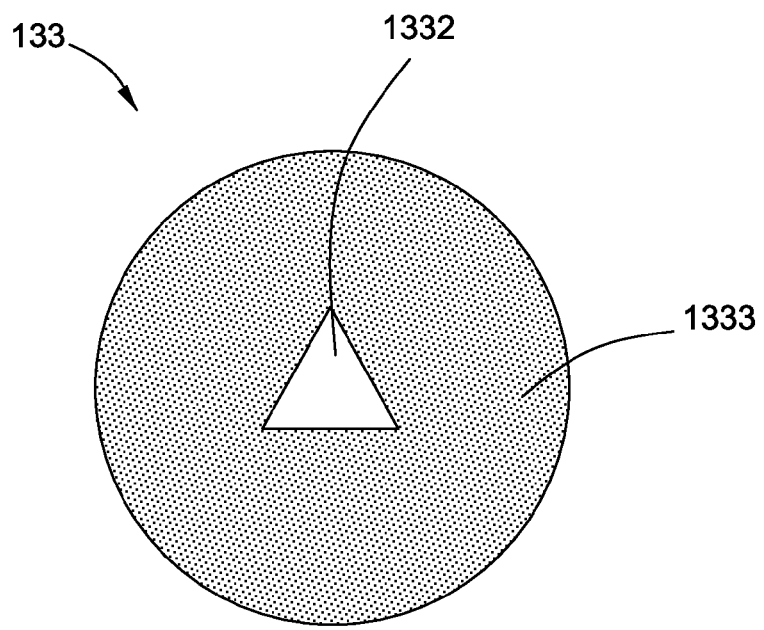

FIGS. 18 and 19 shows two schematic front views of the aperture element of the aperture stop assembly of FIGS. 5-8 in accordance with another two embodiments.

Figure 20:
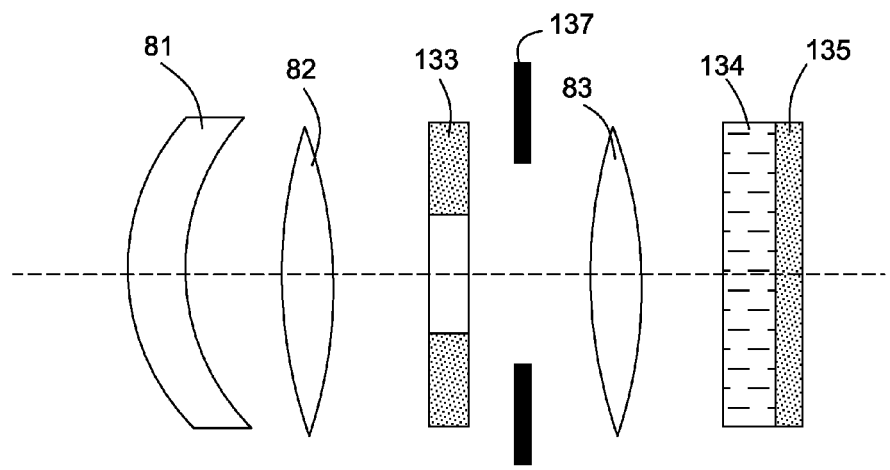
Figure 21:
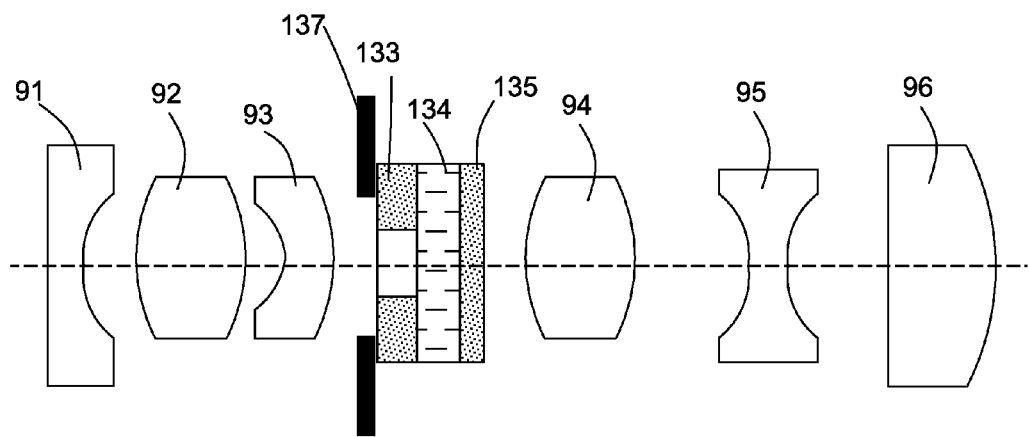

FIGS. 20 and 21 are two schematic views of two aperture stop assemblies in accordance with two embodiments applied in two different lens groups, respectively.

DETAILED DESCRIPTION

Embodiments disclosed herein relate to an inspection device using an optical imaging system for visually inspecting a target having variable positions with respect to the inspection device. The optical imaging system includes a birefringent element, a light modulating element, and a polarizer element. The birefringent element is configured for decomposing un-polarized light into first linear polarized light and second linear polarized light under different refractive indexes to respectively form a first focal length and a second focal length in the optical imaging system. The light modulating element is configured for modulating a state of polarization the first and second linear polarized light in response to control signals. The polarizer element is configured for filtering out one of the modulated first and second linear polarized light for creating a single image.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect.

Figure 1:
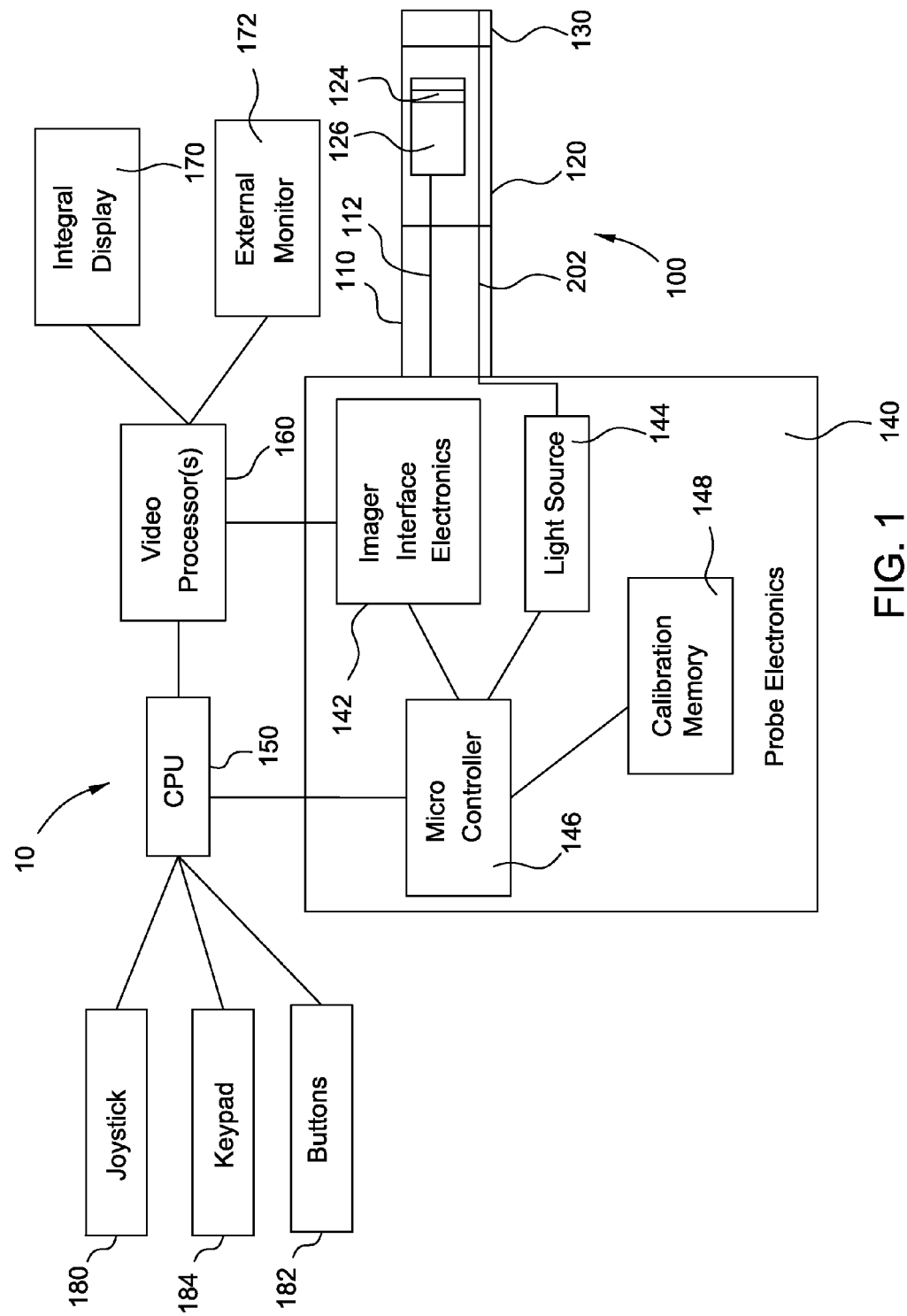
FIG. 1 is a block diagram of an inspection device in accordance with an exemplary embodiment of the present disclosure.

FIG. 1 illustrates a block diagram of an inspection device 10 in accordance with an exemplary embodiment. The inspection device 10 may include a device such as a borescope, a videoscope, a fiberscope, an endoscope, a healthcare microscope, a cellphone camera, a machine vision camera, or a security monitoring camera for example, and may be used in applications such as industrial applications and medical applications. In one implementation, the inspection device 10 may be used for remote visual inspection in a hard-to-access area. Data obtained by the inspection device may be used for condition monitoring and detection of defects such as edge breaks, scratches, and surface finish pits, for example.

Referring to FIG. 1, the inspection device 10 may include an elongated probe 100 including an insertion tube 110 and a head assembly 120 disposed at the distal end of the insertion tube 110. The insertion tube 110 may be a flexible, tubular section through which all interconnects between the head assembly 120 and probe electronics 140 are passed. The elongated probe 100 may include an optical imaging system 130 (or "tip") for guiding and focusing light reflected or diffused from the target onto an imager 124. The light reflected or diffused from the target may be generated from a light source 144 and may be transmitted through a fiber optic bundle 202. The light source 144 may include a white light source and may include any appropriate light source for a probe such as a mercury or metal halide arc lamp, halogen lamp, laser/phosphor system, or LED based light source, for example.

The imager 124 may include multiple pixels formed in multiple rows and columns and is configured to generate image signals in the form of analog voltages representative of light incident on each pixel of the imager 124. In one embodiment, the image signals are then propagated through imager hybrid 126, which provides electronics for signal buffering and conditioning, to an imager harness 112, which provides wires for control and video signals between the imager hybrid 126 and imager interface electronics 142. The imager interface electronics 142 may include power supplies, a timing generator for generating imager clock signals, an analog front end for digitizing the imager video output signal, and a digital signal processor for processing the digitized imager video data into a more useful video format.

The imager interface electronics 142 may optionally be included within the probe electronics 140, which provide a collection of functions for operating the inspection device 10. The probe electronics 140 may also include a calibration memory 148, which stores the calibration data for the probe 100. A microcontroller 146 may also be included in the probe electronics 140 for communicating with the imager interface electronics 142 for determining and setting gain and exposure settings, storing and reading calibration data from the calibration memory 148, controlling the light delivered to the target, and communicating with a central processing unit (CPU) 150 of the inspection device 10.

In addition to communicating with the microcontroller 146, the imager interface electronics 142 can also communicate with one or more video processors 160. The video processor 160 can receive video signals from the imager interface electronics 142 and output signals to various monitors, including an integral display 170 or an external monitor 172. The integral display 170, in one embodiment, may include a liquid crystal display (LCD) screen built into the inspection device 10 for displaying various images or data (e.g., the image of the target, menus, cursors, and measurement results) to an inspector. The external monitor 172 may include a video monitor or a computer-type monitor connected to the inspection device 10 for displaying various images or data.

The video processor 160 may provide and receive commands, state information, streaming video, still video images, and graphical overlays to and from the CPU 150 and may be comprised of FPGAs, DSPs, or any other processing elements which provide functions such as image capture, image enhancement, graphical overlay merging, distortion correction, frame averaging, scaling, digital zooming, overlaying, merging, flipping, motion detection, and video format conversion and compression.

The CPU 150 may be used to manage the user interface by receiving input via a joystick 180, buttons 182, and/or a keypad 184, in addition to providing a host of other functions, including image, video, and audio storage and recall functions, zoom and focus control, system control, and measurement processing.

The joystick 180 can be manipulated by the user to perform such operations as menu selection, cursor movement, slider adjustment, and articulation control of the probe 100, and may include a push-button function. The buttons 182 and/or keypad 184 also can be used for menu selection and providing user commands to the CPU 150 (e.g., freezing or saving a still video image).

Figure 2:
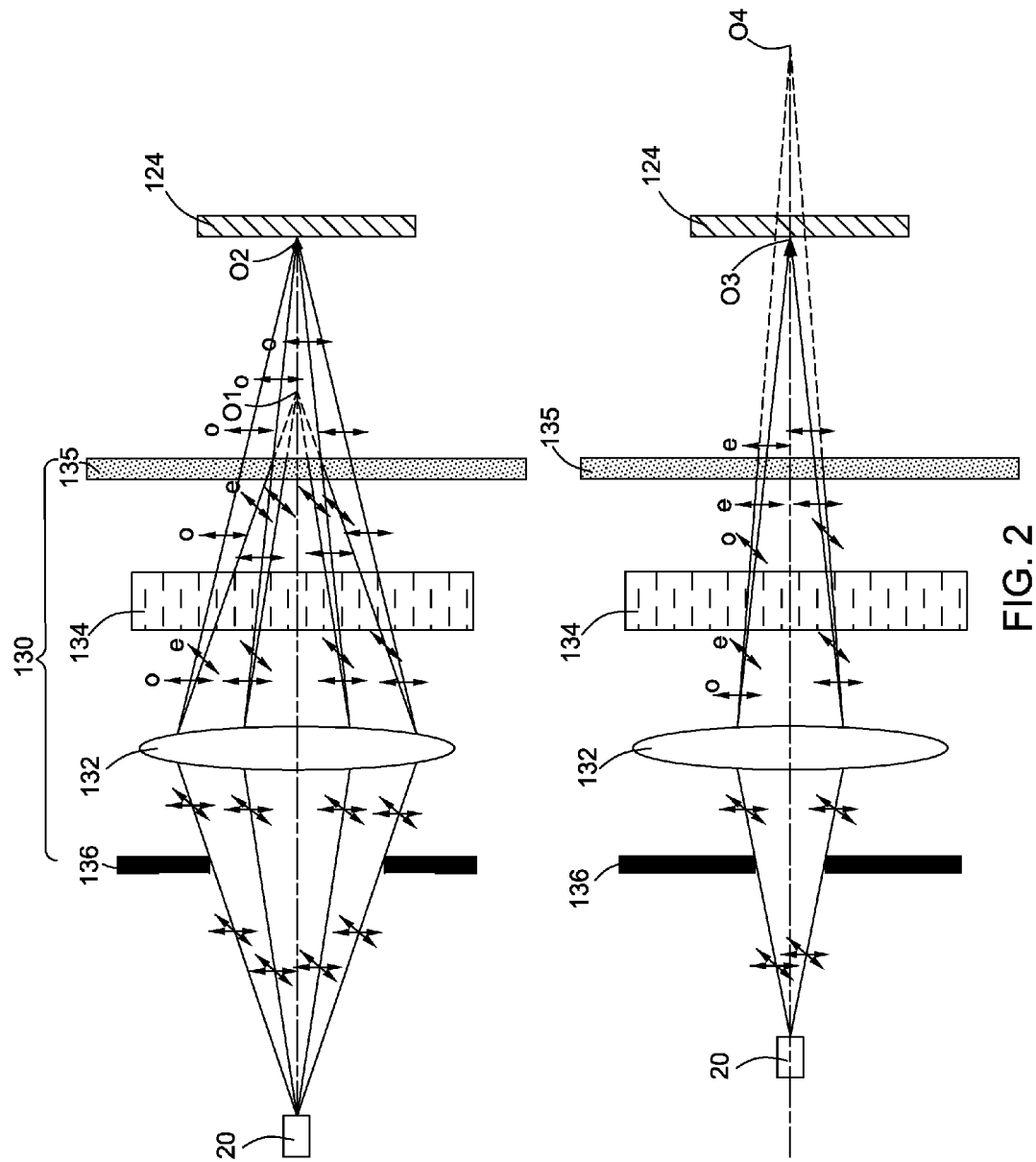
FIG. 2 is a schematic view to show an optical imaging system and an imager in accordance with a first exemplary embodiment applied in two different states, respectively.

FIG. 2 illustrates a schematic view to show the optical imaging system 130 and the imager 124 of the inspection device 10 of FIG. 1 in accordance with a first exemplary embodiment applied in two different states, respectively. In one embodiment, the optical imaging system 130 may include a lens group having a variable aperture stop element 136 and a birefringent element 132, a light modulating element 134, and a polarizer element 135. In one implementation, as a non-limiting example, the variable aperture stop element 136, the birefringent element 132, the light modulating element 134, and the polarizer element 135 are separately constructed in the optical imaging system 130. In other implementations, two or more optical elements in the optical imaging system 130 may be integrated together to form a single element. For example, in some embodiments, the light modulating element 134 and the polarizer element 135 may be integrated together. The variable aperture stop element 136, the birefringent element 132, the light modulating element 134, and the polarizer element 135 are arranged substantially perpendicular to an optical axis. In some implementations, one or more optical elements may be further disposed between the variable aperture stop element 136 and the birefringent element 132, or between the birefringent element 132 and the light modulating element 134, or between the light modulating element 134 and the polarizer element 135, or any other appropriate location.

In one implementation, the optical imaging system 130 may be removably mounted to the distal end of the head assembly 120 (shown in FIG. 1). In other implementations, the optical imaging system 130 may be fixed to the head assembly 120. When a target 20 to be inspected varies its position, the optical imaging system 130 is capable of being switched to converge light reflected or diffused from the target 20 with different focal lengths. Because the focal length of the optical imaging system 130 will vary with respect to the birefringent element material's refractive index under different state of polarization of light, the optical imaging system 130 can be switched to converge light with different refractive powers. Depending on the positions of the target 20 and the quality of the image formed by the converged light, the focal length of the optical imaging system 130 may be manually switched or automatically switched, so that both a far field target 20 (shown in the upper part of FIGS. 2-4) and a near field target 20 (shown in the lower part of FIGS. 2-4) can be formed with clear images. As used herein, "near field" refers to a target having a relatively short distance with respect to an optical imaging system. In one embodiment, as a non-limiting example, the near field may cover a range of 7 mm through 35 mm. As used herein, "far field" refers to the target having a relatively long distance with respect to an optical imaging system. In one embodiment, as a non-limiting example, the far field may cover a range of 35 mm through 450 mm.

With continuing reference to FIG. 2, in one implementation, the birefringent element 132 is used for converging light to the imager 124, such that an image of the target 20 can be formed by the converged light. In one embodiment, the birefringent element 132 may include one or more birefringent lens(es), which can refract light of different state of polarization under different refractive indexes correspondingly. In one implementation, the birefringent lens(es) may use Yttrium orthovanadate (YVO4) to refract the light. YVO4 is a typical type of birefringent material, which can exhibit different refractive indexes with respect to incident light having different incident angle and state of polarization with respect to the optical axis thereof. For example, un-polarized light incident to the YVO4 can be decomposed into extra-ordinary beam (e-beam) and ordinary beam (o-beam) light. In other implementations, the birefringent lens may use other materials such as α-BBO Crystal ($BaB_2O_4$), Calcite, Lithium Niobate, Quartz, or a combination of such materials. In other embodiments, the birefringent element 132 may be any appropriate means which can decompose light of different polarization states under different refractive indexes correspondingly, such as one or more polarization splitting prism elements configured to create a different optical path length for different state of polarization of light.

With continuing reference to FIG. 2, the light modulating element 134 is used for modulating or changing state of polarization of the linear polarized light in response to control signals. In one implementation, the light modulating element 134 may include liquid crystal. When linear polarized light passes through the light modulation element 134, the state of polarization of the linear polarized light can be changed by driving the liquid crystal with different voltages. For example, an incident light beam to the light modulating element 134 may be in vertical linear state of polarization. When the liquid crystal is driven with a voltage of 0 volts, the emergent light beam from the light modulating element 134 is changed into horizontal linear state of polarization. When the liquid crystal is driven with a voltage larger than a threshold value such as 5 volts, the emergent light from the light modulating element 134 remains in vertical linear state of polarization. In other implementations, the light modulating element 134 may be not limited to liquid crystal. For example, a Faraday rotator, an optoelectric crystal, and a wave plate are other alternative elements which may be used to modulate the state of polarization of incident light to the light modulating element 134. The optical imaging system 130 is changed from a first state to a second state through changing the modulating states of the light modulating element 134.

With continuing reference to FIG. 2, the polarizer element 135 is used for filtering out linear polarized light in one fixed state of polarization, such as horizontal linear state of polarization. In one implementation, the polarizer element 135 may filter out linear polarized light based on an optical reflection mechanism. In this implementation, the polarizer element 135 may be selected from a group consisting of a polymer polarizing film, a grating polarizer, a Glan-Taylor polarizer, a Glan-Thompson polarizer, and a piece stack polarizer, for example. In another implementation, the polarizer element 135 may filter out linear polarized light based on an optical refraction mechanism. In this implementation, the polarizer element 135 may be selected from a group consisting of a Rochon polarizer and a Wollaston polarizer, for example. In yet another implementation, the polarizer element 135 may filter out linear polarized light based on an optical absorption mechanism. In this implementation, the polarizer element 135 may include a polymer polarizing film, for example.

Referring again to the upper part of FIG. 2 (first state), in operation, the optical imaging system 130 may be operated to capture images of the target 20 in the far field. In this case, the optical imaging system 130 may be switched to operate in a first focusing mode having a first focal length. The light source 144 shown in FIG. 1 may be switched on to emit light. The light may be transmitted directly or indirectly by fiber optic bundles to the target 20 so as to illuminate the target 20. The light reflected or diffused from the target 20 passes through the aperture stop element 136 with an appropriate aperture size through mechanical control, such as motor control. The light passing through the aperture stop element 136 is decomposed to e-beam light and o-beam light with respect to the birefringent element 132, which are respectively focused at two different focus points O1 and O2. In this state, the imager 124 is located at the focus point O2. In other embodiments, the two linear polarized light beams decomposed from the birefringent element 132 may not be e-beam light and o-beam light, they can be any two linear polarized light beams as long as they are two linear polarized light beams under different refractive indexes, which can form two different focus points O1 and O2.

In one embodiment, the o-beam light emerged from the birefringent element 132 maybe vertical linear polarized light, and the e-beam light emerged from the birefringent element 132 maybe horizontal linear polarized light. In the drawings, the vertical linear polarized light is shown as an upright short double arrow line " ↕ ", and the horizontal linear polarized light is shown as an oblique short double arrow line " ⤢ ". The light modulating element 134 does not modulate the state of polarization of the linear polarized light passing through it in this state, for example, when the light modulating element 134 is driven with 5 volts. In one embodiment, the polarizer element 135 is used for filtering out the horizontal linear polarized light, thus the e-beam light is filtered out by the polarizer element 135, and the o-beam light passes through the polarizer element 135. Because the focus point O2 of the o-beam light is at the position of the imager 124, the image of the target 20 in the far field can be formed for inspection in the imager 124.

Referring again to the lower part of FIG. 2 (second state), the optical imaging system 130 may be further operated to capture images of the target 20 in the near field. In this case, the optical imaging system 130 may be switched to operate in a second focusing mode having a second focal length. The light reflected or diffused from the target 20 pass through the aperture stop element 136 with an appropriate aperture size through mechanical control. The light passing through the aperture stop element 136 is decomposed to e-beam light and o-beam light by the birefringent element 132, which are respectively focused at two different focus points O3 and O4. In this state, the imager 124 is located at the focus point O3 (the same as the focus point O2). In one embodiment, the o-beam light emerging from the birefringent element 132 maybe vertical linear polarized light, and the e-beam light emerging from the birefringent element 132 maybe horizontal linear polarized light. The light modulating element 134 modulates 90 degrees of the state of polarization of the linear polarized light passing through it in this state, for example, when the light modulating element 134 is driven with 0 volts. Thus, the o-beam light emerging from the light modulating element 134 is modulated to horizontal linear polarized light, and the e-beam light emerging from the light modulating element 134 is modulated to vertical linear polarized light. In one embodiment, the polarizer element 135 is used for filtering out the horizontal linear polarized light, such that the o-beam light is filtered out by the polarizer element 135, and the e-beam light passes through the polarizer element 135. Because the focus point O3 of the e-beam light is at the position of the imager 124, the image of the target 20 in the near field can be formed for inspection in the imager 124. In other embodiment, the polarizer element 135 also can be used for filtering out the vertical linear polarized light.

As described above, the optical imaging system 130 may be manually or automatically switched between a first focusing mode and a second focusing mode. With regard to automatically switching the optical imaging system 130 between the dual-focus modes, in one implementation, the position of the target 20 may be detected by a detecting device (not shown). When the position of the target 20 is detected and determined to be in the far field, the inspection device 10 can send control signals to switch the optical imaging system 130 in the first focusing mode in which a relatively longer focal length is used for converging light and obtaining the image of the target 20 in the far field. When the position of the target 20 is detected and determined to be in the near field, the inspection device 10 can send control signals to switch the optical imaging system 130 in the second focusing mode in which a relatively shorter focal length is used for converging light and obtaining the image of the target 20 in the near field.

In this illustrated embodiment of FIG. 2, the aperture size of the variable aperture stop element 136 may be controlled by a mechanical means such as a motor (not shown). Due to its mechanical nature, the control process may produce vibrations which can affect performance of the optical imaging system 130. In addition, the switch speed from one state of the variable aperture stop element 136 to another state can be relatively slow under such mechanical control. Furthermore, the mechanical controls require additional space in the optical imaging system 130, which may affect cost as well as how compact the optical imaging system 130 can be. An aperture element 133 (shown and described with respect to in FIGS. 3 and 4), which is not controlled by mechanical means, can function as a substitute for the variable aperture stop element 136.

Figure 3:
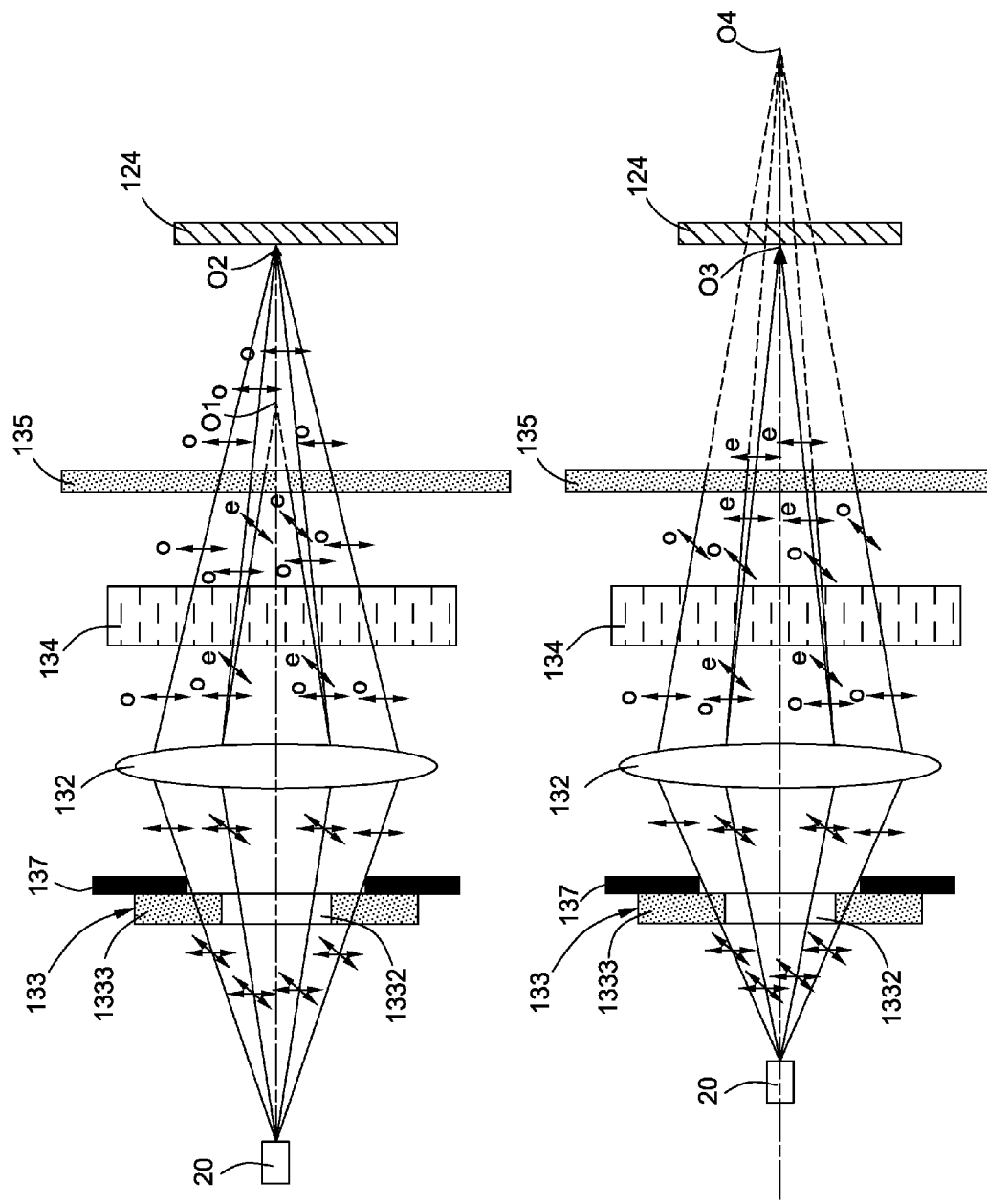
FIG. 3 is a schematic view to show an optical imaging system and an imager in accordance with a second exemplary embodiment applied in two different states, respectively.

FIG. 3 illustrates a schematic view to show the optical imaging system 130 and the imager 124 of the inspection device 10 of FIG. 1 in accordance with a second exemplary embodiment applied in two different states. The difference between FIG. 2 and FIG. 3 is that the embodiment illustrated in FIG. 3 applies an aperture element 133 to replace the variable aperture stop element 136. Accordingly, the above mentioned issues related to mechanical control of the variable aperture stop element 136 can be eliminated by using the aperture element 133. In one embodiment, the aperture element 133 includes a polarizer part 1333 and defines an aperture part 1332 in the center of the polarizer part 1333. The aperture part 1332 acts as a first aperture and the polarizer part 1333 together with the aperture part 1332 (namely the entire aperture element 133) acts as a second aperture. As shown, the size of the first aperture part 1332 is less than the size of the second aperture 133. For achieving a better performance, another fixed aperture stop element 137 may be supplied in the optical imaging system 130, such as located between the aperture element 133 and the birefringent element 132. The aperture size of the aperture stop element 137 is larger than the aperture part 1332 of the aperture element 133. In other embodiments, the fixed aperture stop element 137 also can be located between other two elements of the optical imaging system 130, and also can be omitted. The polarizer part 1333 of the aperture element 133 is used for filtering out linear polarized light in one fixed state of polarization, such as a horizontal state of polarization. The material of the polarizer part 1333 of the aperture element 133 can be selected according to the material of the polarizer element 135 mentioned above and is thus not described again. In other embodiments, the polarizer part 1333 of the aperture element 133 also can be can used for filtering out linear polarized light in another fixed state of polarization, such as a vertical state of polarization.

Referring again to the upper part of FIG. 3 (first state), in operation, the optical imaging system 130 may be operated to capture images of the target 20 in the far field. In this case, the optical imaging system 130 may be switched to operate in a first focusing mode having a first focal length similar to the upper part of FIG. 2. The light reflected or diffused from the target 20 passes through the aperture part 1332 of the aperture element 133, and only the vertical linear polarized light reflected or diffused from the target 20 passes through the polarizer part 1333 of the aperture element 133. The light passing through the aperture part 1332 of the aperture element 133 is decomposed to e-beam light and o-beam light with respect to the birefringent element 132, which are respectively focused at two different focus points O1 and O2. The vertical linear polarized light passing through the polarizer part 1333 of the aperture element 133 is only o-beam light. In this state, the imager 124 is located at the focus point O2. The light modulating element 134 does not modulate the state of polarization of the linear polarized light passing through it in this state, for example, when the light modulating element 134 is driven with 5 volts. In one embodiment, the polarizer element 135 is used for filtering out the horizontal linear polarized light, thus the e-beam light is filtered out by the polarizer element 135, and the o-beam light pass through the polarizer element 135. Because the focus point O2 of the o-beam light is at the position of the imager 124, the image of the target 20 in the far field can be formed for inspection in the imager 124. Accordingly, in this state, the aperture element 133 acts as a relatively large aperture stop used in the optical imaging system 130 without any mechanical control. In one embodiment, the polarizer part 1333 of the aperture element 133 and the polarizer element 135 filter out the linear polarized light which have the same state of polarization. In other embodiments, the polarizer part 1333 of the aperture element 133 and the polarizer element 135 also can filter out the linear polarized light which have different state of polarization, such as have orthogonal state of polarization.

Referring again to the lower part of FIG. 3 (second state), in contrast, the optical imaging system 130 may be further operated to capture images of the target 20 in the near field. In this case, the optical imaging system 130 may be switched to operate in a second focusing mode having a second focal length similar to the lower part of FIG. 2. The light reflected or diffused from the target 20 passes through the aperture part 1332 of the aperture element 133, and only the vertical linear polarized light reflected or diffused from the target 20 passes through the polarizer part 1333 of the aperture element 133. The light passing through the aperture part 1332 of the aperture element 133 is decomposed to e-beam light and o-beam light with respect to the birefringent element 132, which are respectively focused at two different focus points O3 and O4. The vertical linear polarized light passing through the polarizer part 1333 of the aperture element 133 is only o-beam light. In this state, the imager 124 is located at the focus point O3 (the same as the focus point O2). The light modulating element 134 modulates 90 degrees of the state of polarization of the linear polarized light passing through it in this state, for example, when the light modulating element 134 is driven with 0 volts. Thus, the o-beam light emerged from the light modulating element 134 is modulated to horizontal linear polarized light, and the e-beam light emerged from the light modulating element 134 is modulated to vertical linear polarized light. In one embodiment, the polarizer element 135 is used for filtering out the horizontal linear polarized light, such that the o-beam light is filtered out by the polarizer element 135, and the e-beam light passes through the polarizer element 135. Because the focus point O3 of the e-beam light is at the position of the imager 124, the image of the target 20 in the near field can be formed for inspection in the imager 124. Accordingly, in this state, the aperture element 133 acts as a relatively small aperture stop used in the optical imaging system 130 without any mechanical control.

Because the aperture element 133 does not need to be controlled by any mechanical means such as motors, it can reduce vibrations due to the lack of mechanical control. Furthermore, the switch speed from one state to another state of the optical imaging system 130 is very fast also due to no mechanical control. Moreover, because the mechanical means is omitted, the optical imaging system 130 can be designed to a more compact configuration.

Figure 4:
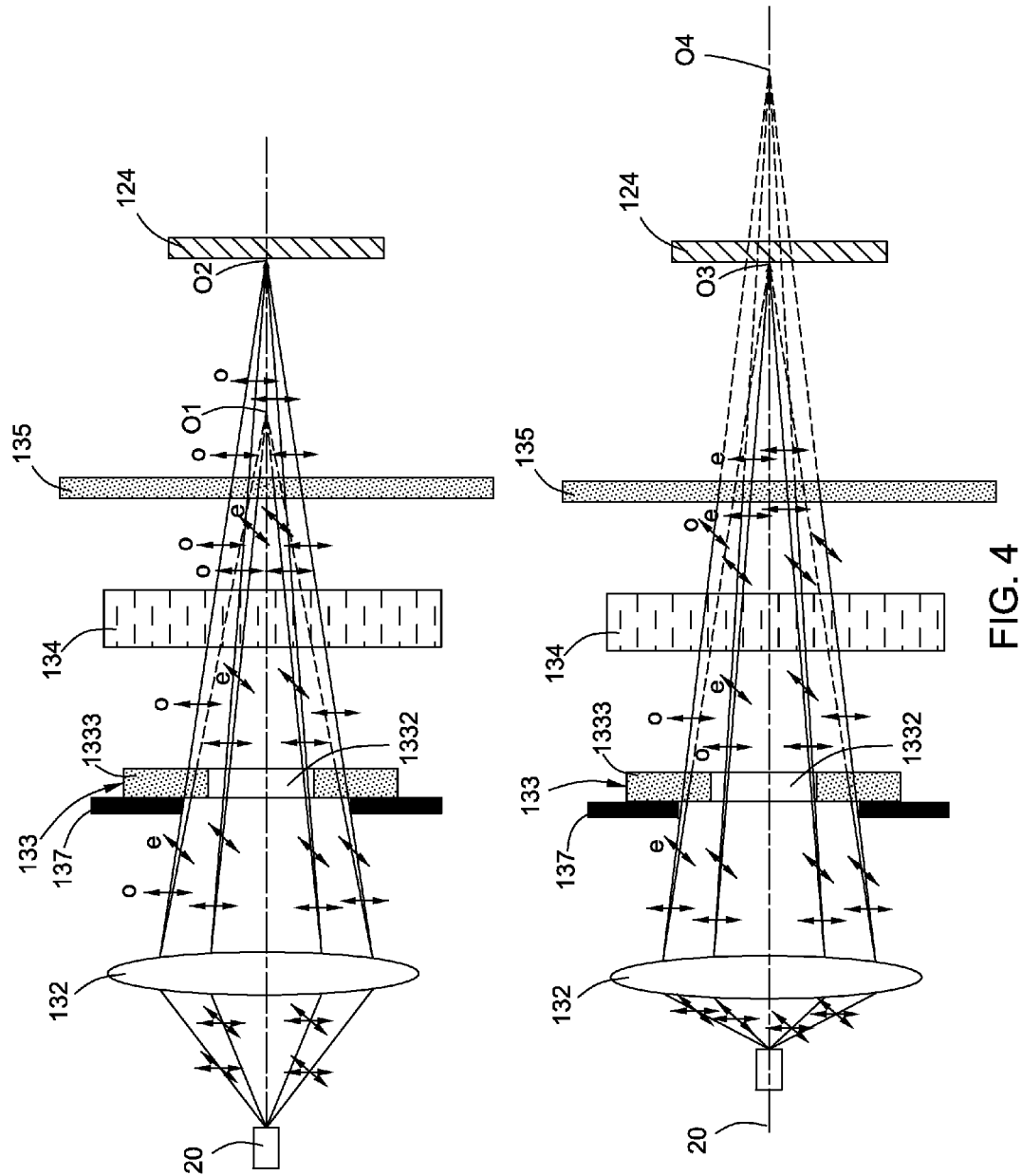
FIG. 4 is a schematic view to show an optical imaging system and an imager in accordance with a third exemplary embodiment applied in two different states, respectively.

FIG. 4 illustrates a schematic view to show the optical imaging system 130 and the imager 124 of the inspection device 10 of FIG. 1 in accordance with a third exemplary embodiment applied in two different states, respectively. The difference between FIG. 3 and FIG. 4 is that the locations of the birefringent element 132 and the aperture element 133 are interchanged. It is understood that the working processes of the two embodiments of FIGS. 3 and 4 are similar, and thus the working process of the embodiment of FIG. 4 is not described again. In other embodiments, the aperture element 133 instead can be located between the light modulating element 134 and the polarizer element 135 to operate under similar working processed as previously described, and is therefore not described again. Therefore, according to above disclosed embodiments, the positions of the elements of the optical imaging system 130 can be adjusted flexibly. Additionally, the aperture element 133, the light modulating element 134, and the polarizer element 135 can be operated as an aperture stop assembly to apply in any appropriate lens group to accomplish a two-mode aperture stop element without mechanical control, which will be described hereinafter.

FIGS. 5 and 6 respectively show two working states of the aperture stop assembly in accordance with an exemplary embodiment when the incident light is propagated towards to the aperture element 133. FIGS. 7 and 8 respectively show two working states of the aperture stop assembly in accordance with an exemplary embodiment when the incident light is propagated towards to the polarizer element 135. To assist in explaining the two working states of the aperture stop assembly, aperture lines A are introduced, wherein the aperture lines A are the lines extended from the circumference of the aperture part 1332. The light propagated within the aperture line A is labeled as 22, and the light propagated outside of the aperture line A is labeled as 21 in FIGS. 5-8.

With continuing reference to FIG. 5 (first state), according to optical theory, non-polarized light can be decomposed into vertical linear polarized light and horizontal linear polarized light. In this state, the light modulating element 134 does not modulate the state of polarization of the linear polarized light passing through it, for example, when the light modulating element 134 is driven with 5 volts. After passing through the aperture element 133, the light 22 does not change, and the light 21 is changed to vertical linear polarized light. After passing through the light modulating element 134, the light 22 also does not change, and the light 21 remains vertical linear polarized light. After passing through the polarizer element 135, the light 22 is changed to vertical linear polarized light, and the light 21 remains vertical linear polarized light. Thus, the aperture stop assembly in this state acts as a relatively large aperture stop element.

With continuing reference to FIG. 6 (second state), in the illustrated state, the light modulating element 134 modulates 90 degrees of the state of polarization of the linear polarized light passing through it, for example, when the light modulating element 134 is driven with 0 volts. After passing through the aperture element 133, the light 22 does not change, and the light 21 is changed to vertical linear polarized light. After passing through the light modulating element 134, the light 22 also does not change, and the light 21 is changed to horizontal linear polarized light. After passing through the polarizer element 135, the light 22 is changed to vertical linear polarized light, and the light 21 is filtered out. Thus, the aperture stop assembly in this state acts as a relatively small aperture stop element.

With continuing reference to FIG. 7 (first state), in this state, the light modulating element 134 does not modulate the state of polarization of the linear polarized light passing through it. After passing through the polarizer element 135, the light 22 and 21 are changed to vertical linear polarized light. After passing through the light modulating element 134, the light 22 and 21 do not change. After passing through the aperture element 133, the light 22 and 21 do not change. Thus, the aperture stop assembly in this state acts as a relatively large aperture stop element.

With continuing reference to FIG. 8 (second state), in this state, the light modulating element 134 modulates 90 degrees of the state of polarization of the linear polarized light passing through it. After passing through the polarizer element 135, the light 22 and 21 is changed to vertical linear polarized light. After passing through the light modulating element 134, the light 22 and 21 are changed to horizontal linear polarized light. After passing through the aperture element 133, the light 22 does not change, and the light 21 is filtered out. Thus, the aperture stop assembly in this state acts as a relatively small aperture stop element.

With continuing reference to FIG. 9, for example, the light modulating element 134 may be liquid crystal, and triggered by two electrodes 1342 and 1344. In one non-limiting embodiment, the two electrodes 1342 and 1344 are respectively electrically coupled to two terminals of an alternating current (AC) power supply 30 with a switch K in series. When the switch K is turned on, the two electrodes 1342 and 1344 have a voltage difference therebetween, sufficient to trigger the light modulating element 134 in the first state (shown in FIGS. 5 and 7). In one embodiment, the voltage difference is 5 volts. When the switch K is turned off, the two electrodes have zero volts voltage difference therebetween, which triggers the light modulating element 134 in the second state (shown in FIGS. 6 and 8). In other embodiments, the light modulating element 134 can also be triggered by other kinds of control circuits, such as a direct current power supply, a processor, and a micro control unit, and so on.

Figure 11:
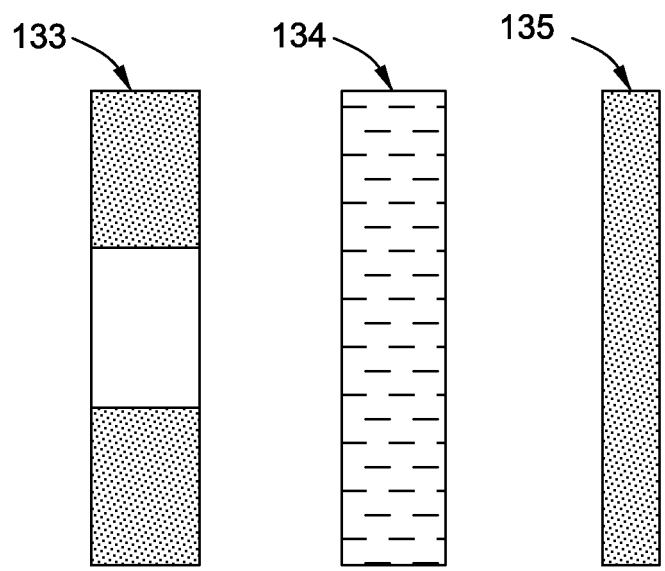
Figure 12:
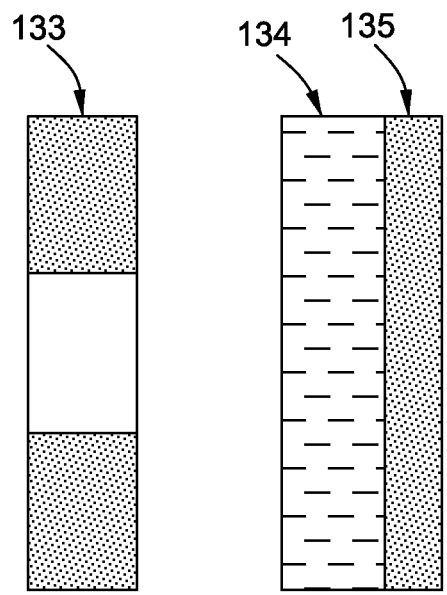
Figure 13:
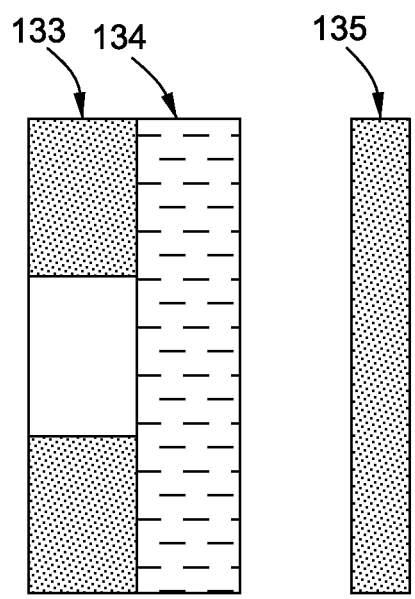

In non-limiting embodiments, the aperture element 133, the light modulating element 134, and the polarizer element 135 can be separately constructed in an optical imaging system, or two of them can be integrated together to form a single element, or all of them can be integrated together to form a single element. For example, referring to FIG. 10, the aperture element 133, the light modulating element 134, and the polarizer element 135 are integrated together. Referring to FIG. 11, the aperture element 133, the light modulating element 134, and the polarizer element 135 are separately constructed. Referring to FIG. 12, the light modulating element 134 and the polarizer element 135 are integrated together and then separately constructed with the aperture element 133. Referring to FIG. 13, the aperture element 133 and the light modulating element 134 are integrated together and then separately constructed with the polarizer element 135.

For a variety of reasons including manufacturing or mounting requirements, one or more transparent substrates 138 can be attached to appropriate places in the aperture stop assembly. For example, with continuing reference to FIGS. 14 and 15, a single transparent substrate 138 or two transparent substrates 138 can be attached to one side or two opposite sides of the aperture element 133, respectively. With continuing reference to FIG. 16, two transparent substrates 138 can be arranged on the outer sides of the light modulating element 134 and one of the transparent substrates 138 can be arranged between the light modulating element 134 and the polarizer element 135. Although FIGS. 14-16 only show three examples of the arrangements of the transparent substrates 138, they are not intended to be limiting and other arrangements are contemplated. The transparent substrates 138 may be made of any appropriate transparent material to allow light beams pass through it without any change. For example, the transparent substrates may be made of glass.

Referring to FIG. 17, in this illustrated embodiment, the shape of the aperture part 1332 of the aperture element 133 is round. In other embodiments, the shape of the aperture part 1332 also can be, but need not be limited to, rectangular and triangle, for example (see FIGS. 18 and 19).

The aperture stop assembly (133, 135, 135) also can be applied in other optical imaging systems, and are not limited to the embodiments mentioned in this disclosure. For example, referring to FIG. 20, the aperture stop assembly can be used in a lens group and may further include a plano-concave lens 81 and two double-convex lenses 82 and 83. The aperture stop assembly may be divided in two parts, the aperture element 133 and the integrated light modulating element 134 and polarizer element 135, for example. The lens 81, the lens 82, the aperture element 133, the lens 83, and the integrated light modulating element 134 and polarizer element 135 may be located side by side, for example. It is understood that the aperture stop assembly can be switched to the above-described two different states as required.

For another non-limiting example, referring to FIG. 21, the aperture stop assembly can be used in a lens group and may further include two plano-concave lens 91, 93, two double-convex lenses 92, 94, a double-concave lens 95, and a convex lens 96. The aperture stop assembly may be integrated together, for example. In one embodiment, the lens 91, the lens 92, the lens 93, the aperture stop assembly, the lens 94, the lens 95, and the lens 96 may be located side by side, for example. It is understood that the aperture stop assembly can be switched to the above two different states as required. In non-limiting embodiments, the fixed aperture stop element 137 also can be arranged in the lens groups shown in FIGS. 20 and 21, to further provide a fixed aperture stop support.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An optical imaging system, comprising:
   a birefringent element configured for decomposing unpolarized light into first linear polarized light and second linear polarized light under different refractive indexes to respectively form a first focal length and a second focal length in the optical imaging system;
   a light modulating element configured for modulating a state of polarization of the first and second linear polarized light in response to control signals; and
   a polarizer element configured for filtering out one of the modulated first and second linear polarized light for creating a single image.

2. The optical imaging system of claim 1, further comprising a variable aperture stop element, wherein the variable aperture stop element is configured to be switched into at least a first aperture size and a second aperture size corresponding to the first focal length and the second focal length of the optical imaging system.

3. The optical imaging system of claim 1, wherein the light modulating element modulates the state of polarization of the first and second linear polarized light by 90 degrees and 0 degrees in two different states, respectively.

4. The optical imaging system of claim 1, wherein the birefringent element comprises a birefringent lens or a polarization splitting prism.

5. The optical imaging system of claim 1, wherein the light modulating element is selected from a group consisting of a Faraday rotator, an optoelectric crystal, a wave plate, and a liquid crystal.

6. The optical imaging system of claim 1, wherein the polarizer element is selected from a group consisting of a polymer polarizing film, a grating polarizer, a Glan-Taylor polarizer, a Glan-Thompson polarizer, a piece stack polarizer, a Rochon polarizer, a Wollaston polarizer.

7. The optical imaging system of claim 1, further comprising an aperture element comprising a polarizer part and defining an aperture part in the center of the polarizer part, wherein the polarizer part is configured for filtering out linear polarized light in a fixed state of polarization, the aperture element is located between a target and the birefringent element or between the birefringent element and the light modulating element.

8. The optical imaging system of claim 7, wherein the aperture element is selected from a group consisting of a polymer polarizing film, a grating polarizer, a Glan-Taylor polarizer, a Glan-Thompson polarizer, and a piece stack polarizer.

9. A method for providing multiple focal lengths for inspecting a target having variable positions with respect to an optical imaging system employed in an inspection device, the method comprising:
decomposing un-polarized light reflected or diffused from the target into first linear polarized light and second linear polarized light under different refractive indexes to respectively form a first focal length and a second focal length in the optical imaging system;
modulating a state of polarization of the first and second linear polarized light in response to control signals; and
filtering out one of the modulated first and second linear polarized light for creating a single image.

10. The method of claim 9, wherein modulating a state of polarization of the first and second linear polarized light in response to control signals comprises:
modulating the state of polarization of the first and second linear polarized light by 90 degrees in a first state; and
modulating the state of polarization of the first and second linear polarized light by 0 degrees in a second state.

11. An aperture stop assembly, comprising:
an aperture element comprising a polarizer part and defining an aperture part in the center of the polarizer part, the polarizer part configured for filtering out linear polarized light in a first fixed state of polarization;
a light modulating element configured for modulating a state of polarization of linear polarized light in response to control signals;
a polarizer element configured for filtering out linear polarized light in a second fixed state of polarization; and
wherein the light modulating element is located between the aperture element and the polarizer element.

12. The aperture stop assembly of claim 11, wherein the light modulating element modulates the state of polarization of linear polarized light by 90 degrees and 0 degrees in two different states, respectively.

13. The aperture stop assembly of claim 11, wherein the first fixed state of polarization and the second fixed state of polarization are the same, or orthogonal to each other.

14. The aperture stop assembly of claim 11, wherein the light modulating element is selected from a group consisting of a Faraday rotator, an optoelectric crystal, a wave plate, and a liquid crystal.

15. The aperture stop assembly of claim 11, wherein the polarizer element and the aperture element are selected from a group consisting of a polymer polarizing film, a grating polarizer, a Glan-Taylor polarizer, a Glan-Thompson polarizer, a piece stack polarizer, a Rochon polarizer, a Wollaston polarizer.

16. The aperture stop assembly of claim 11, wherein two adjacent elements of the aperture element, the light modulating element, and the polarizer element are integrated together, or the aperture element, the light modulating element, and the polarizer element are integrated together.

17. The aperture stop assembly of claim 11, further comprising a fixed aperture stop element.

18. The aperture stop assembly of claim 11, further comprising one or more transparent substrates attached on one or more sides of the aperture element, the light modulating element, or the polarizer element.

19. An aperture element, comprising:
a linear polarizer comprising a polarizer part, the polarizer part configured for filtering out linear polarized light in a fixed state of polarization; and
a first aperture part comprising an aperture through the linear polarizer in the center of the polarizer part, the aperture configured for not changing light propagated within a circumference of the aperture,
wherein the linear polarizer and the first aperture part comprise a second aperture part.

20. The aperture element of claim 19, wherein the size of the first aperture part is smaller than the size of the second aperture part.

* * * * *